United States Patent
Roff

(12) 
(10) Patent No.: US 6,705,939 B2
(45) Date of Patent: Mar. 16, 2004

(54) METHOD AND APPARATUS FOR REDUCING RESPIRATORY ILLNESSES AMONG OCCUPANTS OF BUILDINGS

(76) Inventor: Roger R. Roff, 200 E. Roosevelt St., Dillon, SC (US) 29536

( * ) Notice: Subject to any disclaimer, the term of this patent is extended or adjusted under 35 U.S.C. 154(b) by 0 days.

(21) Appl. No.: 10/275,099

(22) PCT Filed: May 31, 2001

(86) PCT No.: PCT/US01/17651
§ 371 (c)(1),
(2), (4) Date: Nov. 1, 2002

(87) PCT Pub. No.: WO01/91812
PCT Pub. Date: Dec. 6, 2001

(65) Prior Publication Data
US 2003/0207663 A1 Nov. 6, 2003

Related U.S. Application Data
(60) Provisional application No. 60/208,412, filed on May 31, 2000.

(51) Int. Cl.[7] .................................................. F24F 7/00
(52) U.S. Cl. ....................................... 454/185; 165/168
(58) Field of Search ................................ 454/185, 186; 165/168, 169

(56) References Cited

U.S. PATENT DOCUMENTS

| | | | | |
|---|---|---|---|---|
| 2,641,449 A | * | 6/1953 | Antony | ........................ 165/49 |
| 3,576,157 A | * | 4/1971 | Sebald | ........................ 454/185 |
| 3,633,659 A | * | 1/1972 | Ohlsson | ........................ 165/56 |
| 4,287,753 A |   | 9/1981 | Grantham | |
| 4,296,798 A | * | 10/1981 | Schramm | ..................... 165/56 |
| 4,393,633 A | * | 7/1983 | Charniga | .................. 52/302.3 |
| 4,476,921 A | * | 10/1984 | Stubbolo | ..................... 165/48.1 |
| 4,578,912 A | * | 4/1986 | Ericsson | ..................... 52/169.5 |
| 4,800,672 A |   | 1/1989 | Jackson | |
| 4,823,505 A |   | 4/1989 | Jackson | |
| 4,843,786 A | * | 7/1989 | Walkinshaw et al. | ....... 52/169.5 |
| 4,887,521 A |   | 12/1989 | Miettinen | |
| 5,408,759 A |   | 4/1995 | Bass | |
| 5,746,653 A | * | 5/1998 | Palmer et al. | ............... 454/186 |
| 5,761,864 A | * | 6/1998 | Nonoshita | .................. 52/302.3 |
| 5,896,751 A |   | 4/1999 | Wakizaka et al. | |
| 5,950,326 A |   | 9/1999 | Scott | |
| 6,293,120 B1 | * | 9/2001 | Hashimoto | ..................... 62/260 |
| 6,402,612 B2 | * | 6/2002 | Akhtar et al. | ............... 454/186 |
| 2002/0073628 A1 | * | 6/2002 | Dextras | ........................... 52/1 |

FOREIGN PATENT DOCUMENTS

| | | | | |
|---|---|---|---|---|
| JP | 55063335 A | * | 5/1980 | .............. F24F/1/02 |
| JP | 02183031 A | * | 7/1990 | .............. E04B/1/70 |

* cited by examiner

Primary Examiner—Derek Boles
(74) Attorney, Agent, or Firm—Michael A Mann; John B Hardaway, III; Nexsen Pruet Jacobs & Pollard LLC

(57) ABSTRACT

A method and apparatus for preventing the culturing of microorganisms, including molds, mildew, fungus, viruses, bacteria and insects, within the walls (10), ceilings (15) and floors (45) of a building (12) to eliminate these as a source of respiratory illness and fungal disease among the occupants of a building (12). The method comprises circulating drier, cleaner air into the space (24) between the interior surface (18) and exterior surface (20) of the wall (10), ceiling (15) and floor (45) of the building (12). The apparatus includes a pump (28) and a network of piping (26) installed in the walls (10), ceilings (15) and floors (45) and adapted to create a flow of dry air within the them that absorbs moisture which would otherwise promote the culturing of the microorganisms. Preferably, sensors (32) inside the wall (10), ceiling (15) and floor (45) are connected to a controller (30) to activate the pump (28) when the moisture level rises to a predetermined level.

19 Claims, 2 Drawing Sheets

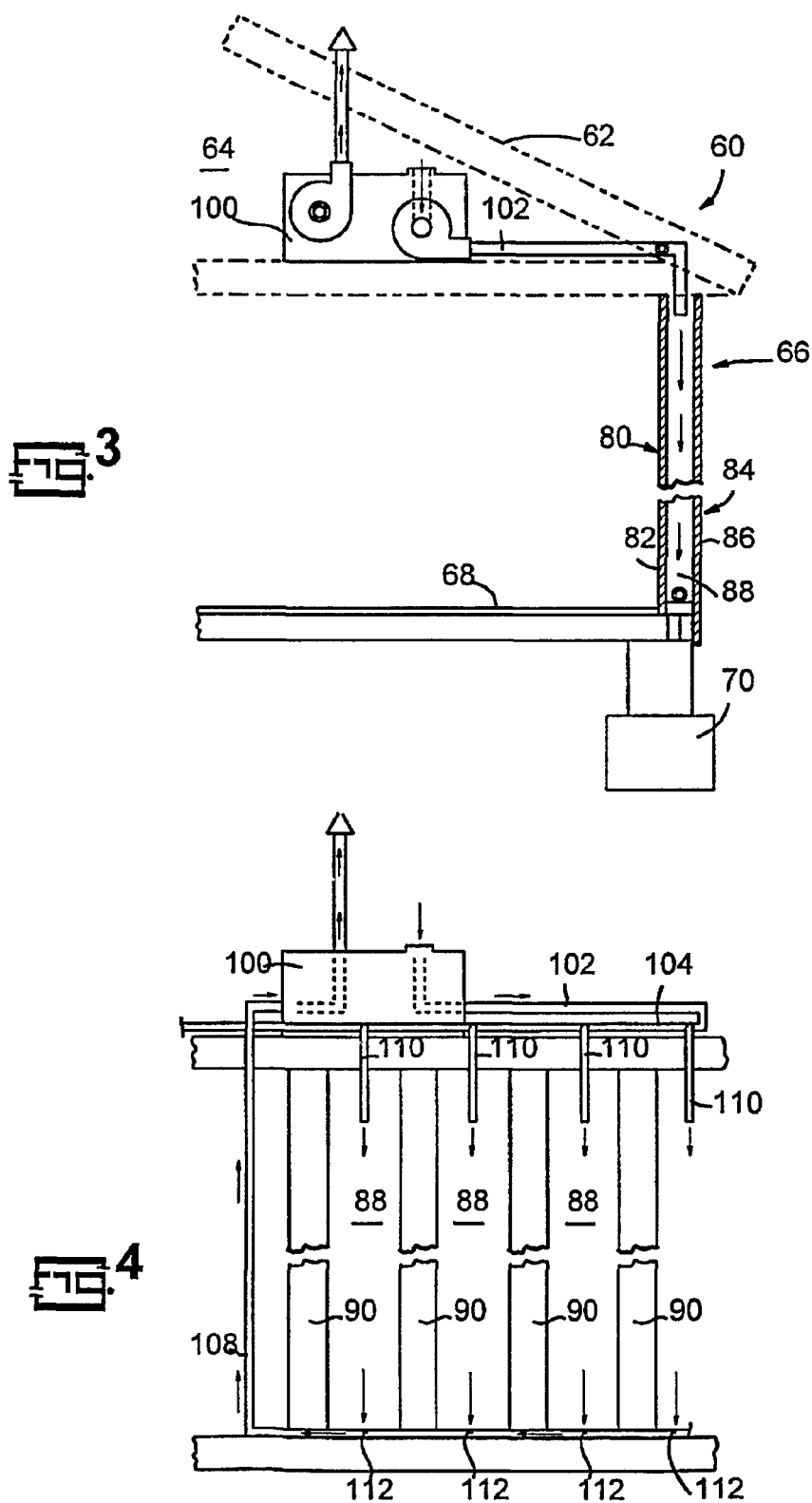

METHOD AND APPARATUS FOR REDUCING RESPIRATORY ILLNESSES AMONG OCCUPANTS OF BUILDINGS

This application claims the benefit of provisional application Ser. No. 60/208,412 filed May 31, 2000.

FIELD OF THE INVENTION

The present invention relates generally to construction techniques and more particularly to the installation of utilities that improve the air within a building for its occupants.

BACKGROUND OF THE INVENTION

Respiratory illnesses and fungal diseases cost hundreds of billions of dollars each year in medical bills and lost productivity. They also claim lives. A significant cause of respiratory illness and fungal disease is the presence in the air of mold, mildew, fungus, viruses, bacteria and insects or their metabolites. Within a building, particularly an older one in which there are occupants who spend a considerable amount of their time, such as a home or an office building, the occupants may be exposed to toxic air laden with mold, mildew, fungus, viruses, bacteria insects and biological contaminants.

The prevalence of this bad air is greater near sources of moisture and in wetter climates, but it is a condition that tends to worsen over time for each building. In particular, the interiors of the walls, floors and ceilings of a home, when the weather is wet, tend to harbor and culture bacteria, molds, mildew, fungus, virus and insects. These interiors of the walls are dark and warm; all they need is moisture to have all the requisite conditions for culturing molds, mildew, fungus, viruses, bacteria and insects.

There remains a need for a method and apparatus for preventing the culturing of molds, mildew, fungus, viruses, bacteria and insects within the walls, ceilings and floors of a building.

SUMMARY OF THE INVENTION

According to its major aspects and briefly recited, the present invention and insects within the walls, ceilings and floors of a building. The method comprises the primary step of circulating fresh, dry air into the spaces between the interior surfaces and exterior surfaces of the walls, ceilings and floors. The apparatus for performing this step is a pump and a network of plastic piping installed in the walls, ceilings and floors and adapted to create a steady flow of dry, clean air within the walls that absorbs moisture which would otherwise promote the culturing of the molds, mildew, fungi, viruses, bacteria, and insects. Preferably, sensors inside the wall are connected to a controller to activate the pump when needed.

In a preferred embodiment, the piping would also facilitate the injection of fumigants including pesticides, fungicides, bactericide, and biocides.

An important feature of the present invention is the monitoring of the moisture level within the interior of the walls. By monitoring the moisture level, the occupants can determine if the conditions for culturing molds, fungi, viruses, bacteria and insects are developing.

Another important feature of the present invention is the piping and pump system. This system allows moisture to be removed before it rises to the level at which culturing conditions occur. Furthermore, it also serves as a vehicle for introducing more aggressive agents for thwarting mold, mildew, fungus, viruses, bacteria, and insects, that might otherwise develop and for venting radon gas and its daughter products.

Still another feature of the present invention is the method of circulating air throughout the spaces in the walls of a building to prevent mold, mildew, fungus, viruses, bacteria and insects from establishing themselves in the walls, ceilings and floors where they can cause respiratory illness and fungal diseases in occupants of the building. By preventing their occurrence, a significant cause of respiratory illness and fungal diseases is reduced or eliminated.

Yet another feature of the present invention is the use of a pump for drawing air from the spaces in the walls and allowing clean, filtered, dry air to be pulled into those spaces rather than pumping air into them where it might create a pressure that would force air through the walls, floors and ceilings and deliver the mold, etc., into the interior rooms of a building.

Other features and their advantages will be apparent to those skilled in construction and in respiratory illnesses from a careful reading of the Detailed Description of Preferred Embodiments, accompanied by the following drawings.

BRIEF DESCRIPTION OF THE DRAWINGS

In the figures,

FIG. 3 is a side, cross sectional view of a building with an air circulation system, according to an alternative, preferred embodiment of the present invention; and FIG. 4 is a front view of the air circulation system of FIG. 3.

DETAILED DESCRIPTION OF PREFERRED EMBODIMENTS

The present invention is a method and apparatus for reducing the incidence of respiratory illness and fungal disease among the occupants of a building by eliminating a source of this type of illness that is associated with the building itself. In particular, respiratory illness and fungal disease are reduced by reducing the amount of mold, mildew, fungus, viruses, bacteria and insects carried by the air inside the building by eliminating the conditions that would allow them to grow inside the walls, ceilings and floors.

Figure 1:
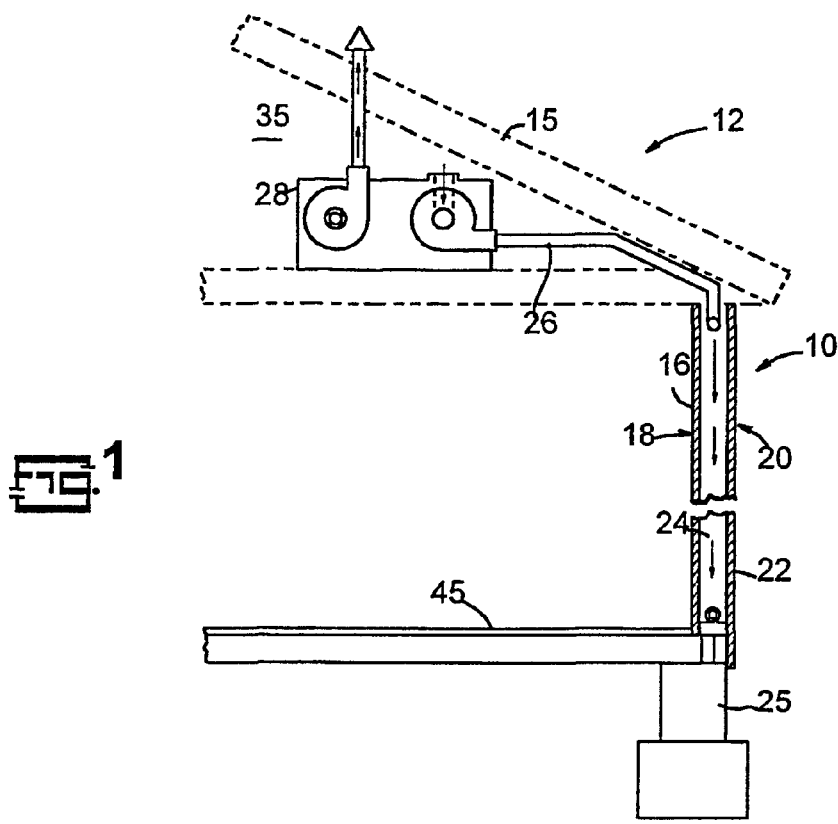
FIG. 1 is a side, cross sectional view of a building with an air circulation system according to a preferred embodiment of the present invention.
Figure 2:
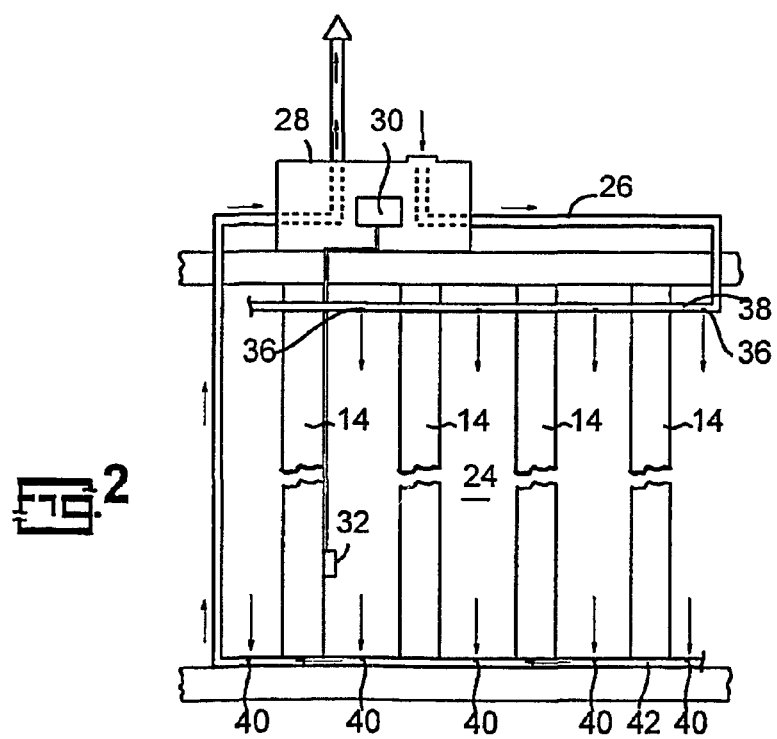
FIG. 2 is a front view of an air circulation system of FIG. 1.

The term "building" generally refers to a home or an office building but may be any building or structure where people spend a lot of time and which has walls formed by two spaced-apart surfaces (such as partitions) or which has walls with spaced-apart interior and exterior surfaces. As illustrated in FIGS. 1 and 2, in conventional building construction, a wall 10 of a building 12, having a ceiling 15, a foundation 25, an attic 35 and a floor 45, is framed in pine "two-by-fours" with two-by-four studs 14, covered with sheet rock 16 that defines an interior surface 18, and has an exterior surface 20 defined by any one (or combination) of a variety of materials 22 on the exterior including insulation, wood, bricks, and vinyl siding. Additional insulation may be installed between the two-by-four studs. However, a space 24 existing between the studs 14 and between the interior and exterior surfaces 18, 20, is dark and warm. All space 24 requires for culturing microorganisms is moisture. If the moisture level in the space is kept below 40%, and the moisture level in the studs is kept below 20%, microorganisms cannot grow. The term "wall" is not intended to be restricted to vertical walls but also includes ceilings and floors where there is a space between two layers that can harbor microorganisms.

The term "microorganisms" will be used herein to include bacteria, molds, fimgi, viruses, mildew, insects and their metabolites. The term "insects" includes cockroaches, fleas, dust mites, and termites, etc.

The present method primarily includes the step of drawing fresh, dry air into the spaces between interior and exterior surfaces 18, 20, of walls 10 and drawing damp air out of the spaces so that the moisture level remains below that required for microorganisms to develop. In particular, the moisture level can be sensed and, when above a threshold level, air at a lower level of moisture can be drawn into space 24. Preferably, as air is pumped out of the spaces from the bottom of the walls, dry air is drawn into the spaces from the top of the wall. Thus, the present method also includes the circulation of dry, preferably filtered, air throughout space 24 within wall 10 and not just its occasional replacement. Air may be circulated continuously, for defined periods at defined intervals of time, or when the relative humidity of the outside air rises above some preselected level. The present method also includes the injection of fumigants into the spaces to kill microorganisms and venting radon gas and its daughter products to the atmosphere. Preferably the air is pumped from the bottom to draw fresh, dry, filtered air in from piping system 26 to replace it using negative pressure in the spaces rather than having air pumped into spaces 24, for positive pressure which could result in a pressure inside wall 10 that could force air through sheet rock 16.

In order to accomplish the present method, a piping system 26 is installed in wall 10 of a building 12 and connected to a pump 28, a controller 30 and a sensor 32. Sensor 32 monitors the moisture content of the air in wall 10 and, when the moisture in space 24 within wall 10 reaches a predesignated level, controller 30, responsive to sensor 32, will active pump 28. Pump 28 draws air from outside building 12, dries and filters in a conditioner, if necessary, and then allows it to be drawn into wall 10 through holes 36 formed in an injection pipe 38. Simultaneously, air from inside wall 10 is pumped out through a hole 40 in an extraction pipe 42 spaced apart from injection pipe 38, creating a flow of air inside wall 10 that removes the existing, moister air and replaces it with drier air.

Periodically, a fumigant selected to eliminate mold, mildew, bacteria and fungus can be injected into piping system 26 to kill any microorganisms that might have otherwise gotten established.

FIGS. 3 and 4 illustrate an alternative, preferred embodiment of the present invention suitable for use in an existing building where the walls are already in existence rather than the embodiment of FIGS. 1 and 2 that is more suited for new construction. FIGS. 3 and 4 show a building 60, having a ceiling 62, an attic 64, a wall 66 a floor 68 and a foundation 70. Wall 66 has an interior surface 80 made of sheet rock 82 and an exterior surface 84 made of any one of a variety of materials 86. Between sheet rock 82 and materials 86 are a series of spaces 88 between a series of studs 90.

A pump system 100 circulates fresh, dry, radon free filtered air through a piping system 102 into space 88 via an injection pipe 104 having plural holes downcomers. An extraction pipe 108 having plural holes 110 allows air from space 88 to be pumped from space 88 and vented to the atmosphere. Injection pipe 104 is connected to space 88 via plural downcomers 110 that run down through a top plate 120 accessible from attic 64 and through holes 112 formed in an extraction pipe 108 is accessible from bottom plate accessible either from a basement or crawl space.

If radon gas and its daughter products are present in the air in a home, particularly in the basement, the present apparatus and method can be used to draw air from the house and vent it to the atmosphere in the same way as described above. The negative pressure from pumping air from the walls and floors draws air into them from the interior spaces and basement and forwards it to an exterior vent. Periodic checking with a sensor such as a Geiger counter that detects radioactivity from radon or its daughter products, in combination with the interior volumetric calculations, can be used to determine the frequency and duration of venting.

What is claimed is:

1. A method for improving air quality inside a building, said building having walls with interior spaces, said method comprising the step of circulating air throughout said interior spaces of said walls of said building, wherein said air being circulated is less than 20% humidity.

2. The method as recited in claim 1, further comprising the step of monitoring humidity in said interior spaces.

3. The method as recited in claim 1, further comprising the step of sensing humidity in said interior spaces, and wherein said circulating step is taken when said humidity rises above a preselected level.

4. The method as recited in claim 3, wherein said preselected level is 20% humidity.

5. The method as recited in claim 1, further comprising the step of injecting fumigants into said interior spaces of said walls to kill microorganisms.

6. The method as recited in claim 1, further comprising the step of filtering said air before circulating said air.

7. The method as recited in claim 1, wherein said circulating step further comprises the step of pumping air out of said interior spaces to allow fresh air to enter said interior spaces.

8. The method as recited in claim 1, wherein said building has ceilings and floors with interior spaces, and wherein said circulating step further comprises circulating said air throughout said interior spaces of said ceilings and floors.

9. A method of improving air quality inside of a building, said building having walls with interior spaces, said method comprising the steps of:

establishing piping in communication with said interior spaces of said walls; and pumping air having a humidity level below 20% into said intenor spaces so that the humidity of said interior spaces is reduced to a level below 20%.

10. The method as recited in claim 9, further comprising the step of injecting a fumigant into said interior spaces to kill microorganisms.

11. The method as recited in claim 10, further comprising the step of sensing humidity in said interior spaces, and wherein said pumping step begins when said humidity rises to approximately 20%.

12. The method as recited in claim 10, further comprising the step of filtering said air before pumping said air into said interior spaces.

13. The method as recited in claim 10, wherein said building has ceilings and floors with interior spaces, and wherein said piping is in communication with said interior spaces of said ceilings and said floors and said pumping steps includes pumping said air into said interior spaces of said ceiling and floors.

14. Apparatus for improving air quality inside a building, said building having walls with interior spaces, said apparatus comprising:
- a pump; and
- a piping system installed in said interior spaces of said walls, said piping system connected to said pump and having plural holes in said piping system through which air, pumped by said pump flows when said pump pumps air, wherein said building has ceilings and floors with interior spaces, and wherein said piping is installed in said interior spaces of said ceilings and floors so that said air can flow within said interior spaces of said ceilings and floors.

15. The apparatus as recited in claim 14, further comprising conditioning means for conditioning air by removing moisture and particulate from air, said conditioning means being connected to said pump so that said conditioning means conditions said air being pumped by said pump before said air enters said wall through said plural holes in said piping system.

16. The apparatus as recited in claim 14, further comprising means for injecting fumigants into said interior spaces to kill microorganisms.

17. The apparatus as recited in claim 14, further comprising:
- sensor means for sensing moisture in said interior spaces of said walls; and
- means for activating said pump when said moisture sensed by said sensor means in said interior spaces rises above a pre-selected level.

18. The apparatus as recited in claim 14, wherein said pump pumps air out of said interior spaces so that fresh air is drawn in by negative pressure in said interior spaces.

19. A method of reducing radon gas inside of a building, said building having walls with interior spaces, said method comprising the steps of:
- establishing piping in communication with said interior spaces of said walls;
- pumping dr air from said interior spaces through said piping to create a negative pressure inside said building and reduce humidity in said interior spaces to less than approximately 20%; and
- venting said air to the atmosphere.

* * * * *